United States Patent
Sathe et al.

(10) Patent No.: US 11,898,134 B2
(45) Date of Patent: Feb. 13, 2024

(54) REACTOR HAVING DYNAMIC SPARGER

(71) Applicant: LanzaTech, Inc., Skokie, IL (US)

(72) Inventors: Mayur Sathe, Skokie, IL (US); Joss Anton Coombes, Chicago, IL (US); Robert John Conrado, Washington, DC (US); Gregory Joseph Morin, Chicago, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

(21) Appl. No.: 18/051,295

(22) Filed: Oct. 31, 2022

(65) Prior Publication Data

US 2023/0132594 A1    May 4, 2023

Related U.S. Application Data

(60) Provisional application No. 63/263,507, filed on Nov. 3, 2021.

(51) Int. Cl.
  *C12M 1/00* (2006.01)

(52) U.S. Cl.
  CPC ............ *C12M 29/06* (2013.01); *C12M 27/20* (2013.01); *C12M 27/22* (2013.01); *C12M 23/40* (2013.01)

(58) Field of Classification Search
  None
  See application file for complete search history.

(56) References Cited

U.S. PATENT DOCUMENTS

| | | |
|---|---|---|
| 2,657,174 A | 10/1953 | Georg |
| 3,220,706 A | 11/1965 | Valdespino |
| 4,043,771 A | 8/1977 | Anand |
| 4,336,224 A | 6/1982 | Siposs |
| 4,415,341 A * | 11/1983 | Echtler ............ B01F 23/23121 95/263 |
| 4,938,865 A | 7/1990 | Jameson |
| 5,173,429 A | 12/1992 | Gaddy |
| 5,593,886 A | 1/1997 | Gaddy |
| 5,951,875 A | 9/1999 | Kanel |

(Continued)

FOREIGN PATENT DOCUMENTS

| | | |
|---|---|---|
| AU | 677542 B2 | 4/1997 |
| CN | 1241149 A | 1/2000 |

(Continued)

OTHER PUBLICATIONS

Kracht et al. "Controlling bubble size using a frit and sleeve sparger." Minerals Engineering 21 (2008) 660-663. (Year: 2008).*

(Continued)

*Primary Examiner* — William H. Beisner

(57) ABSTRACT

Systems and methods relating to dynamic spargers for generating fine bubbles within reactors such as biological and chemical reactors. A sparger system is positioned within a reactor and comprises a support plate, multiple annular shrouds engaged with the support plate, and spargers positioned within the annular shrouds defining a gap between an interior surface of the annular shroud and an exterior surface of the corresponding sparger. Liquid flows through the defined gap between an interior surface of the annular shroud and an exterior surface of the sparger. Acceleration of the liquid through the gap shears bubbles at the exterior surface of the sparger creating bubbles or fine bubbles.

12 Claims, 5 Drawing Sheets

(56) References Cited

U.S. PATENT DOCUMENTS

| | | |
|---|---|---|
| 6,358,483 B1 | 3/2002 | Trott |
| 6,368,819 B1 | 4/2002 | Gaddy |
| 8,143,037 B2 | 3/2012 | Zahn |
| 8,251,228 B2 | 8/2012 | Clayton |
| 9,327,251 B2 | 5/2016 | Li |
| 9,593,598 B2 | 3/2017 | Bapat |
| 2006/0116531 A1 | 6/2006 | Wonders et al. |
| 2007/0254965 A1 | 11/2007 | Boer |
| 2009/0035848 A1 | 2/2009 | Hickey |
| 2010/0002534 A1 | 1/2010 | Zimmerman |
| 2010/0080743 A1 | 4/2010 | Cocco |
| 2010/0193408 A1 | 8/2010 | Jameson |
| 2014/0212937 A1 | 7/2014 | Li |

FOREIGN PATENT DOCUMENTS

| | | |
|---|---|---|
| GB | 2504505 A | 2/2014 |
| JP | 2010247132 A | 11/2010 |
| KR | 100802204 B1 | 2/2008 |
| KR | 20190013145 A | 2/2019 |
| WO | 2002008438 A2 | 1/2002 |
| WO | 2004018067 A2 | 3/2004 |
| WO | 2008028055 A2 | 3/2008 |
| WO | 2008115080 A1 | 9/2008 |
| WO | 2009064200 A2 | 5/2009 |
| WO | 2011129775 A1 | 10/2011 |

OTHER PUBLICATIONS

Smith et al. "Bubble Column Reactors for Wastewater Treatment. 2. The Effect of Sparger Design on Sublation Column hydrodynamics in the homogeneous Flow Regime." Ind. Eng. Chem. Res. 1996, 35, 1700-1710. (Year: 1996).*

International Search Report issued in corresponding International Application No. PCT/NZ2014/00009) dated Aug. 7, 2014, 4 pages.

Abrini, J. Naveau, H. & Nyns, E.J., Archives of Microbiology, (1994), 161, 345-351.

Bredwell et al., Mass Transfer Properties of Microbubbles, Part 1: Experimental Studies, Biotechnol. Prog., (1998), 14, 31-38.

Kalaga, Dinesh V., et al. "Scale-up of a downflow bubble col. Experimental investigations." Chemical Engineering Journal (2020).

Kopke, Michael et al., 2,3 butanediol production by acetogenic bacteria, an alternativeroute to chemical synthesis, using industrial waste gas, Appln. Environ. Microbiol., 17, Jun. 2011, vol. 77, No. 15, pp. 5467-5475.

Lalitha Chockalingam, Mutharasu, "Multiphase Flow Modeling for Design and Optimization of a Novel Down-flow Bubble Column" (2017). LSU Doctoral Dissertations. 4181.

Tanner, R.S. Miller, L.M., & Yang, D., International Journal of Systematic Bacteriology, (1993), 43, 232-236.

Terasaka et al., Chemical Engineering Science, 2011, vol. 66, p. 3172-3179.

Tirado-Acevedo O., Production of Bioethanol from Synthesis Gas Using Clostridium ljungdahlii. PhD thesis, North Carolina State University, 2010.

Tyurin, M. & Kiriukhin, M., Electrofusion of cells of Acetogen *Clostridium* sp. MT 351 with erm(B) or cat in the chromosome, Journal of Biotech Research, (2012), 4:1-12.1-12.

International Search Report and Written Opinion issued in International Application No. PCT/US2022/078967, dated Feb. 28, 2023, 10 pages.

International Search Report and Written Opinion issued in International Application No. PCT/US2022/078973, dated Feb. 27, 2023, 9 pages.

Ong, B.C. et al., "Computed Tomographic Investigation of the Influence of Gas Sparger Design on Gas Holdup Distribution in a Bubble Column", Ind. Eng. Chem. Res., 2009, vol. 48, pp. 58-68.

* cited by examiner

REACTOR HAVING DYNAMIC SPARGER

CROSS REFERENCE TO RELATED APPLICATIONS

This application claims the benefit of U.S. Provisional Patent Application No. 63/263,507, filed Nov. 3, 2021, the entirety of which is incorporated herein by reference.

FIELD

Embodiments described herein generally relate to systems and methods for the injection of gas bubbles into a liquid. In particular, systems and methods disclosed herein generally relate to dynamic spargers for generating and injecting bubbles or fine bubbles into a liquid broth within a chemical or biological reactor. Further, systems and methods are disclosed herein for the injection of gaseous carbon-substrate fine bubbles within a bioreactor containing liquid microorganism cultures that biologically ferment the carbon substrate for the production of a useful product such as ethanol or other chemicals.

BACKGROUND

A sparger is a device that injects gas into a liquid. Gas injected into the liquid from a sparger forms bubbles in the liquid. Conventional systems employing spargers for the generation and injection of gas bubbles into liquids during industrial process are well-known. To maximize the conversion of gas substrates injected into liquids to useful fermentation products in bioreactors, spargers need to produce small bubbles with increased gas flow rates through the sparger. Conventional sparger systems, however, cannot achieve the required small bubble size because bubble size at the sparger increases with increased gas flow rates. As such, what is needed is a sparger system that can generate fine bubbles at higher gas flow rates in bioreactors to achieve high productivity. Additionally, previous "frit and sleeve" sparger systems comprising porous ring (frit) surrounded by a sleeve through which liquid is passed are typically external to reactors resulting in inefficient configurations and increased footprint requirements.

The sparger systems disclosed herein overcome the limitations of previous and conventional reactor systems. Specifically, the sparger system and methods of injecting substrate feed gas into the aqueous broth of a reactor, such as a bioreactor, as disclosed herein, achieves small bubble size, increased gas flow rates through the sparger, and higher superficial gas and liquid velocities for high reactor/bioreactor productivity. Further, the sparger systems disclosed herein are configured entirely within the reactor in contrast to previous systems.

SUMMARY

The following presents a simplified summary of various embodiments described herein. This summary is not an extensive overview and is not intended to identify key or critical elements or to delineate the scope of the claims. The following summary merely presents some concepts in a simplified form as an introductory prelude to the more detailed description provided below.

To overcome limitations in previous systems described above, and to overcome other limitations that will be apparent upon reading and understanding the present specification, embodiments described herein are directed to systems and methods for the efficient injection of bubbles into a liquid contained within biological and chemical reactors.

In one embodiment, the systems disclosed herein relate to injecting bubbles into a liquid. The system may include a support plate, a plurality of annular shrouds engaged with the support plate, and a plurality of spargers positioned within the annular shrouds. In some embodiments the support plate and at least one annular shroud are integrated into a single component. In some embodiments, a gap may be defined between the shroud interior surface and the sparger exterior surface. In certain embodiments, the support plate, the annular shrouds, and the spargers may be positioned completely within the interior of a reactor. In certain embodiments, the length of the spargers may be at least 10 cm, and the width of the gap between the shroud interior surface and the sparger exterior surface may be about 1 mm to about 20 mm. In other embodiments, the support plate, the annular shrouds, and the spargers may be positioned at a top portion or at a bottom portion of the reactor. The plurality of spargers may engage a plurality of headers, and the plurality of spargers may be configured to receive a gas supply from the plurality of headers. In certain embodiments, the plurality of headers may further include a baffle configured to disperse a fluid comprising the liquid and bubbles. In yet other embodiments, the liquid may be at least partially recirculated liquid. In certain embodiments, the support plate further includes a plurality of perforations, and the annular shrouds may be positioned within about 20 degrees of a vertical axis of the reactor. In one embodiment, a plurality of support plates may form multiple layers or levels within the interior of the reactor, and the plurality of support plates may include a plurality of annular shrouds, and a plurality of spargers may be positioned within the plurality of annular shrouds.

In one embodiment, the reactor may be a bioreactor including a liquid growth medium and a substrate comprising at least one C1 carbon source. In certain embodiments, the plurality of spargers may be configured to inject substrate bubbles into the liquid growth medium. In other embodiments, the bioreactor may also include a culture of at least one microorganism in the liquid growth medium, and the culture of at least one microorganism may anaerobically ferment the substrate to produce at least one fermentation product.

In still another embodiment, the systems and methods disclosed herein relate to a method of sparging bubbles into a liquid that may include the steps of sparging gas into a reactor containing a liquid via a plurality of spargers positioned within the reactor and configured to emit bubbles, directing a flow of the liquid across an exterior surface of the spargers via a plurality of annular shrouds within the reactor and surrounding the plurality of spargers, and shearing the bubbles at a surface of the plurality of spargers via the flow of the liquid across the exterior surface of the spargers. In certain embodiments, the method may further include accelerating the flow of the liquid across the exterior surface of the spargers via a gap formed between an interior surface of the annular shrouds and the exterior surface of the spargers. In some embodiments, the accelerated flow of the liquid across the exterior surface of the spargers may have a superficial liquid velocity of at least 0.3 m/s, and the accelerated flow of the liquid across the exterior surface of the plurality of spargers may have a velocity of about 0.3 m/s to about 10 m/s. In still other embodiments, the sheared bubbles may have a diameter of about 0.2 mm to about 2.0 mm, and the superficial velocity of a gas phase in the vessel may be at least 0.03 m/s. In one embodiment, the superficial velocity of the gas phase in the vessel may be about 0.03 m/s to about 0.1 m/s. In yet another embodiment, the bubbles may be substrate bubbles within a bioreactor that may contain a liquid growth medium. In other embodiments, a culture of at least one microorganism in the liquid growth medium may aerobically ferment the substrate to produce at least one fermentation product.

These features, along with many others, are discussed in greater detail below.

BRIEF DESCRIPTION OF THE DRAWINGS

A more complete understanding of embodiments described herein, and the advantages thereof may be acquired by referring to the following description in consideration of the accompanying drawings, in which like reference numbers indicate like features, and wherein.

DETAILED DESCRIPTION

Figure 1:
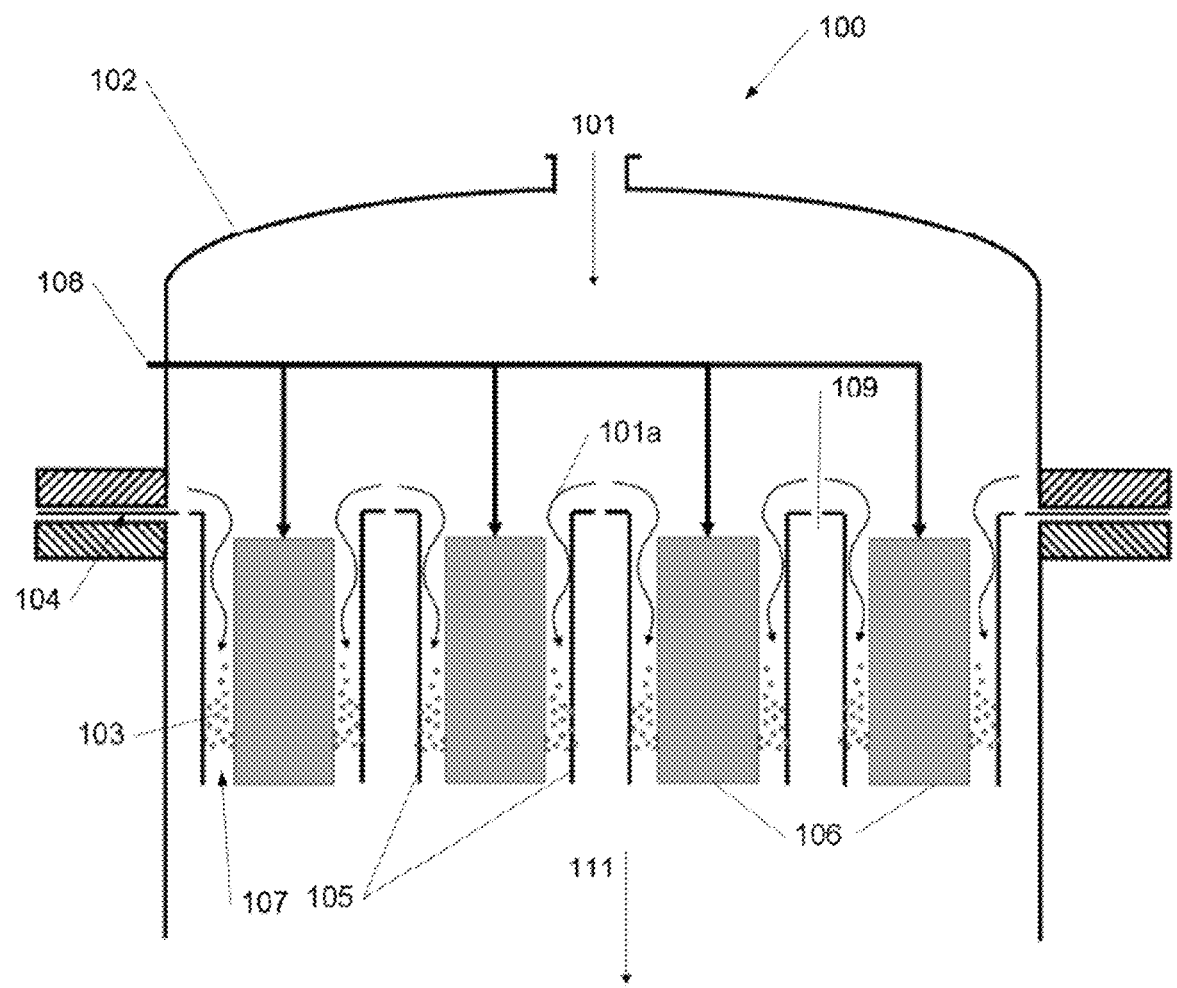
FIG. 1 schematically depicts a dynamic sparger arrangement configured within a reactor showing downflow mode of liquid and bubbles in accordance with one embodiment of the disclosure.

In the following description of the various embodiments, reference is made to the accompanying drawings, which form a part hereof, and in which is shown by way of illustration various embodiments described herein may be practiced. It is to be understood that other embodiments may be utilized, and structural and functional modifications may be made without departing from the scope of the described embodiments. Embodiments described herein are capable of other embodiments and of being practiced or being carried out in various ways. Also, it is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof. The use of the terms "mounted," "connected," "engaged," "fluidly engaged," "coupled," "positioned," "configured," "oriented," and similar terms, is meant to include both direct and indirect mounting, connecting, coupling, positioning, and engaging.

A sparger may comprise a device to introduce a gas into a liquid, injected as bubbles, to agitate it or to dissolve the gas in the liquid. Example spargers may include orifice spargers, sintered spargers, and drilled pipe spargers. In certain configurations, drilled pipe spargers may be mounted horizontally. In other embodiments, spargers may be mounted vertically or horizontally. In some embodiments, the sparger may be a perforated plate or ring, sintered glass, sintered steel, porous rubber pipe, porous metal pipe, porous ceramic, or stainless-steel pipe, drilled pipe, stainless steel drilled pipe, polymeric drilled pipe, etc. The sparger may be of various grades (porosities) or may include certain sized orifices to produce a specific sized bubble or range of bubble sizes.

The systems and methods, as disclosed herein, employ a sparger arrangement for generation of fine bubbles, increasing the gas flow rates through the sparger, and increasing superficial gas velocity and superficial liquid velocity for high reactor productivity. Increasing reactor productivity may be achieved by increasing the amount of gas substrate injected into the liquid broth and available for microbe fermentation, and by increasing the specific interfacial area which is defined as the total surface area of the bubbles in unit volume of the reactor. Specific interfacial area is inversely proportional to the bubble size and directly proportional to gas hold up, where gas hold up is the volume of gas present in a unit volume of fluid having bubbles dispersed therein. Reduction of bubble size by generating fine bubbles increases the specific interfacial area. Increased specific interfacial area enhances gas to liquid mass transfer. In embodiments, where the reactor is a bioreactor, enhanced gas to liquid mass transfer ultimately provides microorganisms with increased amounts of substrate gas to convert into useful fermentation products such as ethanol and other chemicals. Example of systems and methods used to create bubbles include those described in U.S. Pat. No. 9,327,251 hereby incorporated by reference in its entirety for all purposes. Higher reactor productivity may also be achieved by higher gas hold up which is related to increased overall superficial gas velocity and superficial liquid velocity in the reactor. Increased superficial gas velocity and superficial liquid velocity may be used to break or shear sparger bubbles into a desired fine bubble size. In downflow operation, fine bubbles experience a buoyancy force which is less than a drag force imparted by the liquid and hence overall fluid downflow is created to carry the fine bubbles and the liquid downward in the reactor. The fluid downflow helps increase residence time of the microorganisms in the liquid and extends the time for microorganisms to convert fine bubbles of substrate in the bioreactor to desired products.

The sparger system, as disclosed herein, may employ a plate engaged with an array of chimney shroud tubes, or annular shrouds, and cylindrical spargers configured entirely within the reactor. Generally, the inner diameter of the annular shrouds may be slightly larger than the outer diameter of the cylindrical spargers configured within the annular shrouds. As liquid is pumped through the system, the liquid is forced to pass through a restricted space, or gap, between the sparger and the annular shrouds. The liquid is accelerated as it passes through the gap and increases the shear rate provided by the liquid near the surface of the spargers. The increased shear rate reduces the bubble size of gas injected into the liquid from the spargers and creates fine bubbles.

FIG. 1 schematically depicts a bioreactor system 100 comprising reactor 102. Bioreactor system 100 may include any device capable of being used for a fermentation process or a chemical conversion process. Reactor 102 may be a vessel or container in which one or more gas and liquid streams or flows 101 may be introduced for bubble generation and/or fine bubble generation, and for subsequent gas-liquid contacting, gas-absorption, biological or chemical reaction, such as for example, microbial fermentation. The term "microbial fermentation" or "fermentation" or "gas fermentation" and the like may be interpreted as the process which receives one or more gaseous substrates and produces one or more fermentation products through the utilization of one or more C1-fixing microorganisms. The gaseous substrate may be from an industrial process, or may be syngas, or any combination thereof. Syngas may be obtained from a reforming, partial oxidation, or gasification process. A "C1-fixing microorganism" is a microorganism or microbe that produces one or more fermentation products from a C1-carbon source. Typically, the microorganism of the disclosure is a C1-fixing bacterium. The "C1-carbon source" refers a one carbon-molecule that serves as a partial or sole carbon source for the microorganism. For example, the C1-carbon source may comprise one or more of CO, $CO_2$, $CH_4$, $CH_3OH$, or $CH_2O_2$. In an embodiment, the C1-carbon source comprises one or both of CO and $CO_2$. The fermentation process may include the use of one or more bioreactors. The phrases "fermenting," "fermentation process" or "fermentation reaction" and the like, as used herein, are intended to encompass both the growth phase and product biosynthesis phase of the gaseous substrate. Examples of C1-fixing microorganisms may include *Moorella, Clostridium, Ruminococcus, Acetobacterium, Eubacterium, Butyribacterium, Oxobacter, Methanosarcina, Desulfotomaculum, Clostridium autoethanogenum*, and combinations thereof. In one embodiment, the C1 fixing microorganism is *Clostridium autoethanogenum, Clostridium ljungdahlii*, or *Clostridium ragsdalei*.

In some embodiments, liquid 101 is recycled within the system 100. A fluid, as disclosed herein, may include liquid, bubbles, and/or fine bubbles. Fermentation broth or liquid 101 may encompass any mixture of components disclosed herein, for example, a nutrient media and a culture or one or more microorganisms. The fermentation process may utilize the fermentation broth to ferment the substrate gas bubbles or fine bubbles to one or more fermentation products. The bacterial culture may be maintained in an aqueous culture medium that contains nutrients, vitamins, and/or minerals sufficient to permit growth of the microorganism. Bioreactor system 100 may consist of one or more reactors 102 and/or towers or piping arrangements. Suitable bioreactors include, for example, a continuous stirred tank reactor (CSTR), immobilized cell reactor (ICR), trickle bed reactor (TBR), bubble column, gas lift fermenter, static mixer, a circulated loop reactor, a membrane reactor, such as a hollow fiber membrane bioreactor (HFM BR) or other vessel or other device suitable for gas-liquid contact.

Reactor 102 may not be restricted to any specific embodiment, such as height to diameter ratio, or restricted to any specific material and can be constructed from any material suitable to the process such as stainless steel or PVC. Reactor 102 may contain internal components such as one or more static mixers that are common in biological and chemical engineering processing. Reactor 102 may also consist of external or internal heating or cooling elements such as water jackets. Reactor 102 may also be in fluid contact with a pump to circulate or recirculate liquid, bubbles, fine bubbles, and/or fluid 101, 101a, and 111 of system 100. The dimensions of the components of bioreactor system 100, as depicted in FIG. 1, may vary depending upon the required use or process. According to certain embodiments, the diameter of reactor 102 may be, for example, at least, greater than, less than, equal to, or any number in between about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5 to about 20.0 meters. According to other embodiments, the length of reactor 102 may be, for example, at least, greater than, less than, equal to, or any number in between about 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.5, 21.5, 22.0, 22.5, 23.0, 23.5, 24.0, 24.5, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0 to about 50.0 meters.

Figure 2:
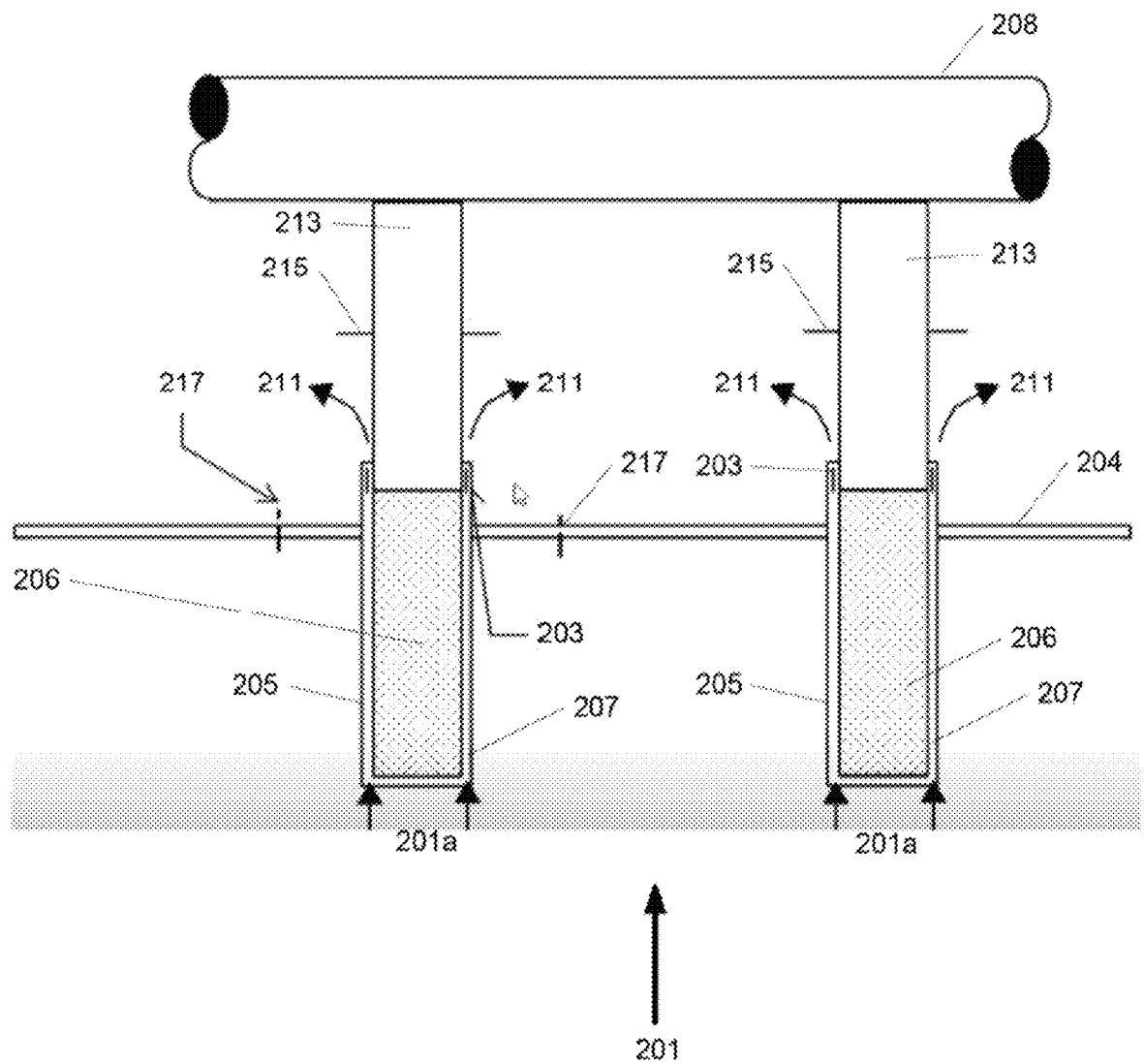
FIG. 2 schematically depicts an alternative dynamic sparger arrangement within a reactor showing upflow mode of liquid and bubbles in accordance with another embodiment of the disclosure.

In reactor 102, the gas and liquid phases, for example, fluid 111, may flow or be circulated in the vertical directions to include generally downward flow or, for example, generally upward flow as shown in FIG. 2. As shown in reactor 102 of FIG. 1, gas and liquid phases in fluid 111 may flow generally downward within reactor 102. The superficial liquid velocity, $V_L$, in the reactor may be calculated by the following equation $V_L=Q_L/A_C$ where $Q_L$ is the volumetric flow rate of the liquid ($m^3/s$), and $A_C$ is the cross-sectional area of the reactor. Therefore, superficial liquid velocity represents velocity of the liquid phase if it occupied the entire cross-sectional area of the reactor. For the same liquid flow rate, the gas flow rate can vary depending on the actual application. Superficial velocity of the gas phase $V_G$ may be determined by the following equation $V_G=Q_G/A_C$ where $Q_G$ is the volumetric flow rate of the gas ($m^3/s$) injected into the liquid from the sparger(s) and $A_C$ is the cross-sectional area of the reactor. Therefore, superficial gas velocity represents velocity of the gas phase if it occupied the entire cross-sectional area of the reactor. In some embodiments, the superficial velocity of the gas phase in the vessel may be at least 0.03 m/s. In other embodiments, superficial velocity of the gas phase in the vessel is about 0.03 m/s to about 0.1 m/s. In still other embodiments, the superficial velocity of the gas phase in the vessel may be, for example, at least, greater than, less than, equal to, or any number in between about 0.01, 0.02, 0.03, 0.04, 0.05, 0.06, 0.07, 0.08, 0.09, 0.10, 0.12, 0.13, 0.14 to about 0.15 m/s. In yet another embodiment, the superficial velocity of the gas phase in the vessel may be, for example, approximately 0.03 to 0.06 m/s. In one embodiment, the superficial liquid velocity may be at least about 0.3 m/s. As discussed above, increasing the superficial gas velocity and the superficial liquid velocity has the beneficial effect of breaking or shearing the sparger bubbles into the desired fine bubble size.

Bioreactor system 100 may include at least one sparger 106 to introduce a gas substrate into liquid 101, injected as bubbles, to agitate the gas or to dissolve the gas in the liquid 101. Sparger 106 may be mounted in a horizontal or a vertical position. In some embodiments, the sparger 106 may be an orifice sparger, sintered sparger, or drilled pipe sparger, a perforated plate or ring, sintered glass, sintered steel, porous rubber pipe, porous metal pipe, porous ceramic or stainless-steel pipe, drilled pipe, stainless steel drilled pipe, or polymeric drilled pipe. Sparger 106 may be of various grades (porosities) or may include certain sized orifices to produce a specific sized bubble. Porosity of spargers are generally designed to avoid weeping which arises when insufficient kinetic energy of the gas flowing through the pores is unable to support the liquid head above the sparger pores. Operating velocity of the gas through the pores is designed substantially higher than weeping velocity to ensure uniform sparging. Sparger 106 may have a length of, for example, at least, greater than, less than, equal to, or any number in between about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, to about 50 cm. The bioreactor system 100 may be adapted to receive a gaseous substrate via header(s) 108 comprising a C1-carbon source injected into the liquid broth 101 as bubbles 103 by sparger 106.

Bioreactor system 100 may include support plate 104. Support plate 104 may be configured to engage at least one annular shroud 105. A diameter of the annular shroud 105 may be larger than the diameter of sparger 106. Thus, sparger 106 may be configured to be positioned inside annular shroud 105 defining a gap or restricted area 107 between the exterior walls of sparger 106 and the interior walls of annular shroud 105. In some embodiments the width of gap 107 is about 1 to 20 mm. In other embodiments, the width of gap 107 may be, for example, at least, greater than, less than, equal to, or any number in between about 0.25, 0.50, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, to about 50 mm.

Spargers 106 and annular shrouds 105 may be positioned entirely within the interior of reactor 102. In some embodiments, support plate 104, annular shrouds 105, and spargers 106 may be positioned at a top or upper portion of reactor 102. Positioning support plate 104, annular shrouds 105, and spargers 106 in an upper portion of reactor 102 may have the additional advantage of decreasing hydrostatic pressure at the top of reactor 102 to facilitate increased gas to liquid mass transfer rates with decreased energy requirements. In some embodiments, the systems and methods disclosed herein achieve gas to liquid mass transfer rates of at least 125 m$^3$/min. In other embodiments, the gas to liquid mass transfer rates may be, for example, at least, greater than, less than, equal to, or any number in between about 100, 105, 110, 115, 120, 125, 130, 135, 140, 145, 150, 155, 160, 165, 170, 175, 180, 185, 190, 195 to about 200 m$^3$/min. Alternatively, support plate 104, annular shrouds 105, and spargers 106 may be positioned at a bottom or lower portion of reactor 102. In still other embodiments, support plate 104, annular shrouds 105, and spargers 106 may be positioned at the upper one-third portion, upper two-thirds portion, or a lower one-third portion of reactor 102. In some embodiments, annular shrouds 105 may be made from standard pipe, seamless tube, welded tube, custom made tube, or combinations thereof. Annular shroud 105 components may be bonded or secured to support plate 104 by shielded metal arc welding, gas tungsten arc welding, gas metal arc welding, flux-cored arc welding, submerged arc welding, electroslag welding, or fabricated by weldless tube-sheet joint rolled in place techniques. In other embodiments, silver soldering may be avoided to prevent damage to microorganisms during fermentation. In still other embodiments, support plate 104 may include perforations 109 to facilitate the removal or draining of solid debris. In certain embodiments, a plurality of support plates 104 may form multiple vertical layers within reactor 102. Each vertical layer of support plates 104 may include a plurality of annular shrouds 105, and a plurality of spargers 106. In still other embodiments, annular shrouds 105 may be positioned generally perpendicular to support plate 104. In other embodiments, the annular shrouds may be positioned, for example, at least, greater than, less than, equal to, or any number in between about 1, 2, 3, 4, 5, 6, 7, 8, 9, 10, 11, 12, 13, 14, 15, 16, 17, 18, 19, 20, 21, 22, 23, 24, 25, 26, 27, 28, 29, to about 30 degrees of a vertical axis of reactor 102.

As shown in FIG. 1, liquid broth 101 enters the top of reactor 102. Gas substrate is injected into liquid 101 within reactor 102 by sparger(s) 106 connected to gas supply/headers 108. At least a portion of the flow of liquid 101 is directed across the exterior surface of spargers 106. In some embodiments, nearly all of the flow of liquid 101 is directed across the exterior surface of spargers 106. As the liquid 101 is forced into gap 107 defined by the annular shroud 105 and the exterior walls of the sparger 106, the liquid is accelerated as it travels across a vertical length of the spargers 106 and the annular shrouds 105. Accelerated liquid 101a shears injected bubbles on the surface of the sparger 106 breaking the injected bubbles into fine bubbles 103. Sheared fine bubbles 103 may have a diameter from about 0.2 to about 2.0 mm. According to another embodiment, the diameter of the fine bubbles may be, for example, at least, greater than, less than, equal to, or any number in between about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 to about 5.0 mm. The accelerated flow of liquid 101a across the exterior surface of the spargers 106 may have a velocity of at least 0.3 m/s. In another embodiments, the accelerated flow of liquid 101a across the exterior surface of the spargers 106 may have a velocity of about 0.3 to about 10 m/s. In other embodiments, the accelerated flow of liquid 101a across the exterior surface of the spargers 106 may have a superficial liquid velocity of, for example, at least, greater than, less than, equal to, or any number in between about 0.1, 0.15, 0.2, 0.25, 0.3, 0.35 1, 2, 3, 4, 5, 6, 7, 8, 9, 10, 11, 12, 13, 14, 15, 16, 17, 18, 19, 20, 21, 22, 23, 24, 25, 26, 27, 28, 29 to about 30 m/s.

According to other embodiments, spargers 106 may be positioned in a bottom portion of reactor 102 or in a middle portion of reactor 102. According to another embodiment, spargers 106 may be oriented in a horizontal position. According to still another embodiment, spargers 106 may be positioned in multiple positions throughout reactor 102 to include the upper, middle, and lower portions of reactor 102. According to yet another embodiment, spargers 106 may be a ring sparger or a drilled-pipe sparger. According to one embodiment, individual spargers 106 and header 108 may be configured as modular components facilitating the ease of reactor construction and/or component replacement, general maintenance, cleaning, or allowing for a scalable reactor system depending upon the requirements. In accordance with other embodiments, multiple levels of spargers 106 and headers 108 may be stacked within reactor 102. In still other embodiments, spargers 106 may be configured to extend vertically below the header 108, or spargers 106 may be configured to extend vertically above the header 108. According to another embodiment, a single level or stack of headers 108 may include, for example, at least, greater than, less than, equal to, or any number in between about 1, 2, 3, 4, 5, 6, 7, 8, 9, 10, 11, 12, 13, 14, 15, 16, 17, 18, 19 to about 20 individual headers 108. In some embodiments, header 108 may be configured as an annular gas supply. In yet another embodiment, one or more fluid distributors (not shown) may be employed so that fluid flow 111 is distributed across reactor 102. In one embodiment, the fluid distributors are positioned near to the fluid exits of gaps 107. The fluid distributors may be impermeable plates or vanes or troughs. The fluid distributors may be attached to a terminal end of spargers 106 and extending below spargers 106 and at least partially across an area below gaps 107.

FIG. 2 depicts an alternative arrangement of the sparger system of FIG. 1. As shown in FIG. 2, the liquid 201 and fluid 211 having both gas phase and liquid phase may flow or be circulated generally in an upward vertical direction in a loop reactor system. The support plate 204 is contained within the reactor. Again, support plate 204 may be configured to engage at least one annular shroud 205. A diameter of the annular shroud 205 may be larger than the diameter of sparger 206. Thus, sparger 206 may be configured to be positioned inside annular shroud 205 defining a gap or restricted area 207 between the exterior walls of sparger 206 and the interior walls of annular shroud 205. Spargers 206 may be fluidly engaged with header 208 through extensions 213 extending therefrom. Header 208 may be configured to receive a gaseous substrate to be injected into liquid broth 201 by spargers 206. Liquid broth 201 may enter from a bottom portion the reactor. At least a portion 201a of liquid 201 may be directed across the exterior surface of spargers 206. In some embodiments, nearly all of the flow of liquid 201 may be directed across the exterior surface of spargers 206. As liquid 201 is forced into gap 207 defined by annular shroud 205 and the exterior walls of sparger 206, liquid 201 is accelerated as it travels vertically upwards through the gap 207. Accelerated liquid 201a shears injected bubbles on the exterior surface of sparger 206 creating fine bubbles 203. Vertical extension 213 extended from the header 208 may include a baffle 215 configured to redirect or deflect the flow of fluid 211 to prevent dead zones of stagnant fluid. Support plate 204 may also include holes or perforations 217 for drainage and circulation for stagnant areas of fluid. In one embodiment, the annular shroud may be disposed within a guide to control adjustment of its concentricity with the sparger (not shown).

As depicted in FIG. 2, the positioning of header 208 above spargers 206 is advantageous because the configuration does not interfere with the upward flow of liquid and bubbles. Additionally, the system components may be modular that allows for ease of construction, maintenance, and replacement of components within the system, to include spargers 106. In some embodiments, header 208 may be permanently installed in the reactor, and spargers 106 may be subsequently attached to vertical extension 213 and/or header 208. Spargers 206 and vertical extensions 213 may be a series of individual pieces/components to be easily transported and inserted into the reactor vessel and then individually connected with the vessel. Like the system depicted in FIG. 1, the system depicted in FIG. 2 may include a plurality of headers 208, and a plurality of support plates 204 may form multiple vertical layers within the reactor. Each vertical layer of support plates 204 may include a plurality of annular shrouds 205, and a plurality of spargers 206 fluidly engaged with a plurality of vertical extensions 213 and header(s) 208. In certain embodiments, the reactor vessel may include, for example, at least, greater than, less than, equal to, or any number in between about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 vertical layers of support plates. In some embodiments, each vertical layer may include, for example, at least, greater than, less than, equal to, or any number in between about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 to about 200 spargers and/or annular shrouds. Again, such a sparger configuration may be employed in reactor systems 100 and 200 described in both FIGS. 1 and 2.

According to other embodiments, spargers 206 may be positioned in a bottom portion of the reactor or in a middle portion of the reactor. According to another embodiment, spargers 206 may be oriented in a horizontal position. According to still another embodiment, spargers 206 may be positioned in multiple positions throughout the reactor to include the upper, middle, and lower portions of the reactor. According to yet another embodiment, spargers 206 may be a ring sparger or a drilled-pipe sparger. According to one embodiment, individual spargers 206 and header 208 may be configured as modular components facilitating the ease of reactor construction and/or component replacement, general maintenance, cleaning, or allowing for a scalable reactor system depending upon the requirements. In accordance with other embodiments, multiple levels of spargers 206 and headers 208 may be stacked within the reactor. In still other embodiments, spargers 206 may be configured to extend vertically below the header 208, or spargers 206 may be configured to extend vertically above the header 208. According to another embodiment, a single level or stack of headers 208 may include, for example, at least, greater than, less than, equal to, or any number in between about 1, 2, 3, 4, 5, 6, 7, 8, 9, 10, 11, 12, 13, 14, 15, 16, 17, 18, 19 to about 20 individual headers 208. In some embodiments, header 208 may be configured as an annular gas supply.

Figure 3:
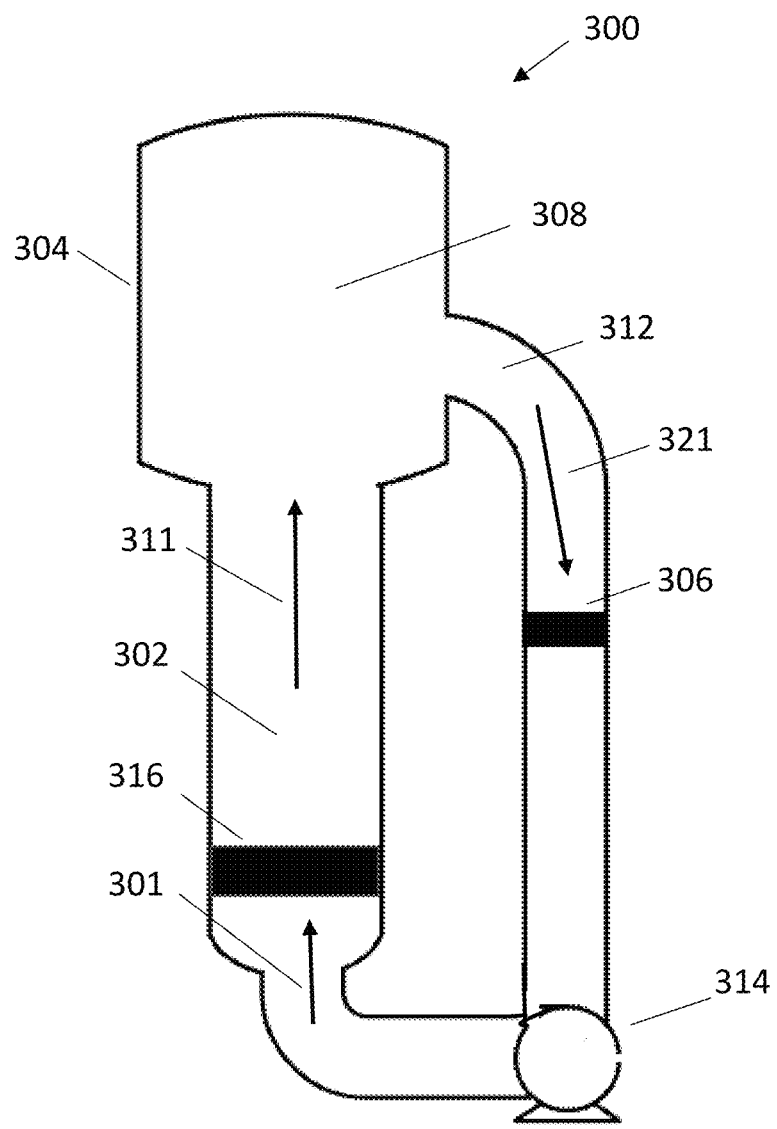
FIG. 3 schematically depicts a bioreactor system including one or more dynamic sparger system arrangements and their various locations within the bioreactor, according to yet another embodiment of the disclosure.

FIG. 3 depicts a loop-style bioreactor system 300 incorporating the sparger-shroud systems and methods disclosed herein. Liquid broth circulating within reactor 304 is injected with gas substrate through one or both of sparger-shroud assemblies 316 and 306. Exemplary details of suitable sparger-shroud assemblies were shown in FIG. 1 and FIG. 2. In one embodiment, at least a portion of the flow of liquid broth 301 flowing into riser section 302 of reactor 304 is forced into gaps defined by the annular shrouds and the exterior walls of the spargers of sparger-shroud assembly 316. Liquid broth 301 is accelerated as it travels through the gap defined by the spargers and the annular shrouds of sparger-shroud assembly 316. The accelerated liquid broth 301 shears injected bubbles on the surface of the spargers thereby creating fine bubbles. Resulting fluid 311 containing the liquid broth and fine bubbles flows upwards in the riser section 302 of reactor 304 and exits riser section 302 into separator section 308. At least a portion of fluid 311 passes out of separator section 308 and into downcomer 312. At this point, fluid 311 may be depleted of gas substrate and form gas substrate depleted liquid broth 321. Optionally, downcomer 312 may include at least one sparger-shroud assembly 306 as disclosed herein. Sparger-shroud assembly 306 located within the downcomer 312 may inject fine bubbles of gas substrate into substrate depleted liquid broth 321 to provide the microorganisms therein with additional substrate and prolong survival. Bioreactor system 300 may include pump 314 to circulate liquid broth 301 and fluid 311 and substrate depleted liquid broth 321 throughout bioreactor system 300.

Figure 4:
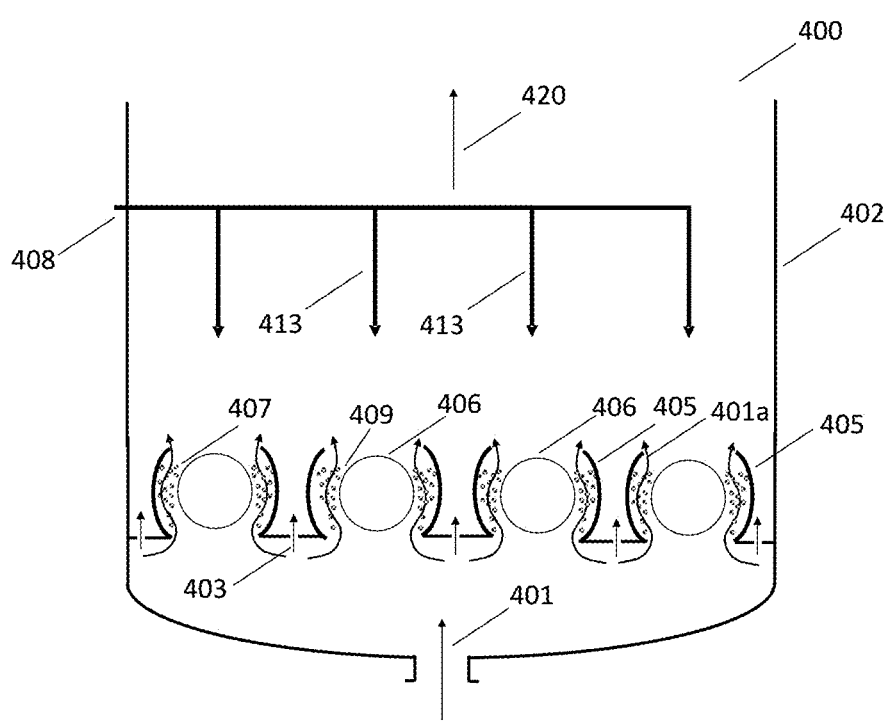
FIG. 4 schematically depicts an alternative dynamic sparger arrangement within a reactor showing horizontally positioned sparges and an upflow mode of liquid and bubbles in accordance with another embodiment of the disclosure.

As shown in FIG. 4, liquid broth 401 enters the bottom of reactor 402. Gas substrate is injected into liquid 401 within reactor 402 by sparger(s) 406 connected to gas supply/headers 408. At least a portion of the flow of liquid 401 is directed across the exterior surface of spargers 406. In some embodiments, nearly all of the flow of liquid 401 is directed across the exterior surface of spargers 406. In other embodiment, portions of liquid flow 401 bypasses the exterior surface of spargers 406 though passages 403. As the liquid 401 is forced into gap 407 defined by the annular shroud 405 and the exterior walls of the spargers 406, the liquid is accelerated as it travels across a circumference or vertical surface of the horizontally positioned spargers 406 and the annular shrouds 405. Accelerated liquid 401a shears injected bubbles on the surface of the spargers 406 breaking the injected bubbles into fine bubbles 409. Sheared fine bubbles 409 may have a diameter from about 0.2 to about 2.0 mm. According to another embodiment, the diameter of the fine bubbles may be, for example, at least, greater than, less than, equal to, or any number in between about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 to about 5.0 mm. Fluid flow comprising the fine bubbles continues in an upflow mode 420. The accelerated flow of liquid 401a across the exterior surface of the spargers 406 may have a velocity of at least 0.3 m/s. In another embodiments, the accelerated flow of liquid 401a across the exterior surface of the spargers 406 may have a velocity of about 0.3 to about 10 m/s. In other embodiments, the accelerated flow of liquid 401a across the exterior surface of the spargers 406 may have a superficial liquid velocity of, for example, at least, greater than, less than, equal to, or any number in between about 0.1, 0.15, 0.2, 0.25, 0.3, 0.35 1, 2, 3, 4, 5, 6, 7, 8, 9, 10, 11, 12, 13, 14, 15, 16, 17, 18, 19, 20, 21, 22, 23, 24, 25, 26, 27, 28, 29 to about 30 m/s.

According to other embodiments, spargers 406 may be positioned in a bottom portion of reactor 402 or in a middle portion of reactor 402. FIG. 4 shows the embodiment where spargers 406 are oriented in a horizontal position. According to still another embodiment, spargers 406 may be positioned in multiple positions throughout reactor 402 to include the upper, middle, and lower portions of reactor 402. According to yet another embodiment, spargers 406 may be a ring sparger or a drilled-pipe sparger. According to one embodiment, individual spargers 406 and header 408 may be configured as modular components facilitating the ease of reactor construction and/or component replacement, general maintenance, cleaning, or allowing for a scalable reactor system depending upon the requirements. In accordance with other embodiments, multiple levels of spargers 406 and headers 408 may be stacked within reactor 402. In still other embodiments, spargers 406 may be configured to extend horizontally spanning the cross section of reactor 402. According to another embodiment, a single level or stack of headers 408 may include, for example, at least, greater than, less than, equal to, or any number in between about 1, 2, 3, 4, 5, 6, 7, 8, 9, 10, 11, 12, 13, 14, 15, 16, 17, 18, 19 to about 20 individual headers 408 or vertical extensions 413. In some embodiments, header 408 may be configured as an annular gas supply.

As further depicted in FIG. 4, the positioning of header 408 above spargers 406 is advantageous because the configuration does not interfere with the upward flow of liquid and bubbles. In FIG. 4, spargers 406 are positioned horizontally within reactor 402. Additionally, the system components may be modular that allows for ease of construction, maintenance, and replacement of components within the system, to include spargers 406. In some embodiments, header 408 may be permanently installed in the reactor, and have vertical extensions 413. Spargers 406, header 408, and vertical extensions 413 may be a series of individual pieces/components to be easily transported and inserted into the reactor vessel and then individually connected with the vessel. The system depicted in FIG. 4 may include a plurality of headers 408, and a plurality of spargers 406 which may form multiple layers within and along the vertical of the reactor. Each layer may include a plurality of annular shrouds 405, and a plurality of spargers 406 fluidly engaged with a plurality of vertical extensions 413 and header(s) 408. In certain embodiments, the reactor vessel may include, for example, at least, greater than, less than, equal to, or any number in between about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 vertical layers of sets of spargers, annular shrouds, and headers. In some embodiments, each vertical layer may include, for example, at least, greater than, less than, equal to, or any number in between about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 to about 200 spargers and/or annular shrouds. Again, such a sparger configuration may be employed in reactor systems 400 and 500 and 600 described in FIGS. 4, 5, and 6.

According to other embodiments, spargers 406 may be positioned in a bottom portion of the reactor or in a middle portion of the reactor. According to FIG. 4 spargers 406 are oriented in a horizontal position. According to still another embodiment, spargers 406 may be positioned in multiple positions throughout the reactor to include the upper, middle, and lower portions of the reactor. According to yet another embodiment, spargers 406 may be a ring sparger or a drilled-pipe sparger. According to one embodiment, individual spargers 406 and header 408 may be configured as modular components facilitating the ease of reactor construction and/or component replacement, general maintenance, cleaning, or allowing for a scalable reactor system depending upon the requirements. In accordance with other embodiments, multiple levels of spargers 406 and headers 408 may be stacked within the reactor. According to another embodiment, a single level or stack of headers 408 may include, for example, at least, greater than, less than, equal to, or any number in between about 1, 2, 3, 4, 5, 6, 7, 8, 9, 10, 11, 12, 13, 14, 15, 16, 17, 18, 19 to about 20 individual headers 408. In some embodiments, header 408 may be configured as an annular gas supply.

Figure 5:
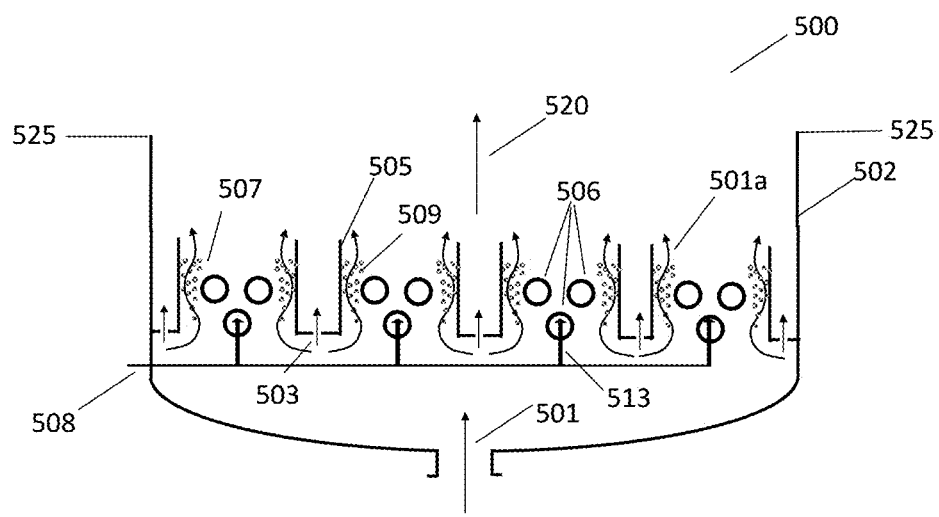
FIG. 5 schematically depicts an alternative dynamic sparger arrangement within a reactor showing bundles of horizontally positioned sparges and an upflow mode of liquid and bubbles in accordance with another embodiment of the disclosure.
Figure 6:
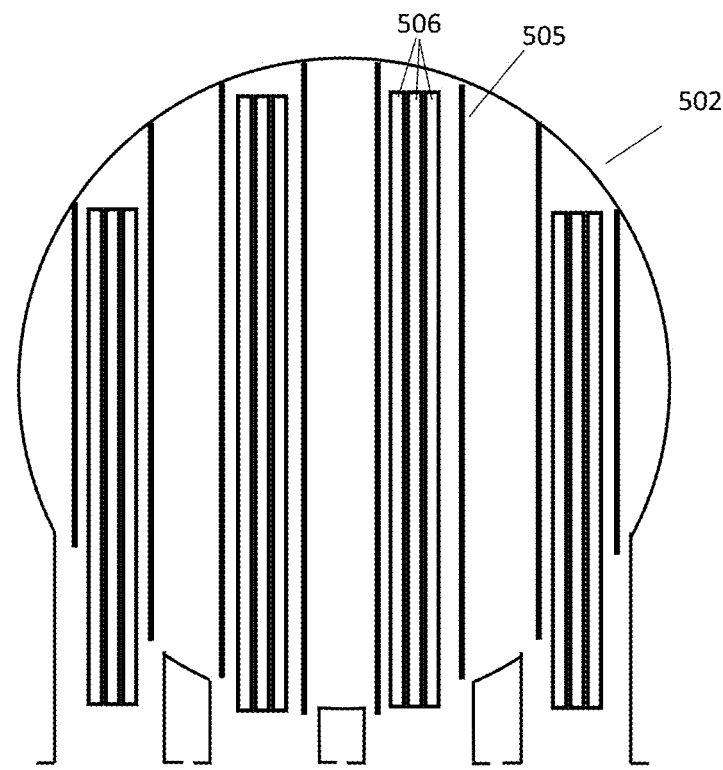
FIG. 6 schematically depicts the device of FIG. 5 in a top view from point 525 of FIG. 5.

FIG. 5, a side view, and FIG. 6, a top view of FIG. 5, depict an embodiment where multiple spargers 506 are positioned within the same annular shroud 505. Having multiple spargers 506 positioned within the same annular shroud 505 allows for reduced piping and header or manifold connections. Similar to FIG. 4, liquid broth 501 enters the bottom of reactor 502. Gas substrate is injected into liquid 501 within reactor 502 by sparger(s) 506 connected to gas supply/headers 508. At least a portion of the flow of liquid 501 is directed across the exterior surface of spargers 506. In some embodiments, nearly all of the flow of liquid 501 is directed across the exterior surface of spargers 506. In other embodiment, portions of liquid flow 501 bypasses the exterior surface of spargers 506 though passages 503. As the liquid 501 is forced into gap 507 defined by the annular shroud 505 and the exterior walls of the spargers 506, the liquid is accelerated as it travels across a circumference or vertical surface of the horizontally positioned spargers 506 and the annular shrouds 505. Accelerated liquid 501a shears injected bubbles on the surface of the spargers 606 breaking the injected bubbles into fine bubbles 509. Fine bubbles are as described above. FIG. 5 and FIG. 6 show three spargers 506 positioned within a single annular shroud 505. The number of spargers positioned within a single annular shroud may vary from about 2 to about 10.

Although the present disclosure has been described in certain specific embodiments, many additional modifications and variations would be apparent to those skilled in the art. It is therefore to be understood that the present disclosure may be practiced otherwise than specifically described without departing from the scope and spirit of the present disclosure. Thus, embodiments of the present disclosure should be considered in all respects as illustrative and not restrictive. Accordingly, the scope of the disclosure should be determined not by the embodiments illustrated, but by the appended claims and their equivalents.

EMBODIMENTS OF THE DISCLOSURE

Embodiment 1. A sparger system for injecting bubbles into a liquid comprising:
a support plate;
a plurality of annular shrouds engaged with the support plate; and
a plurality of spargers positioned within the annular shrouds to define a gap between
an interior surface of the annular shroud and an exterior surface of the corresponding sparger, and
wherein the support plate, the annular shrouds, and the spargers are positioned within the interior of a reactor.

Embodiment 2. The system of embodiment 1 wherein the support plate and the annular shrouds are integrated into a single component.

Embodiment 3. The system of embodiment 1 or 2 wherein two or more spargers are positioned within a single annular shroud.

Embodiment 4. The system of any of embodiments 1 to 3, wherein a length of the spargers is at least 10 cm.

Embodiment 5. The system of any of embodiment 1 to 4, wherein the gap is from about 1 mm to about 20 mm.

Embodiment 6. The system of any of embodiments 1 to 5, wherein the support plate, the annular shrouds, and the spargers are positioned at a top portion or at a bottom portion of the reactor.

Embodiment 7. The system of any of embodiments 1 to 6, wherein the plurality of spargers engage a plurality of headers, and wherein the plurality of spargers are configured to receive a gas supply from the plurality of headers.

Embodiment 8. The system of any of embodiments 1 to 7, wherein the plurality of headers further comprise a baffle configured to disperse a fluid comprising the liquid and bubbles.

Embodiment 9. The system of embodiment 8, wherein the liquid is at least partially recirculated liquid.

Embodiment 10. The system of any of embodiments 1 to 9, wherein the support plate further comprises a plurality of perforations.

Embodiment 11. The system of any of embodiments 1 to 10, wherein the annular shrouds are positioned within about 20 degrees of a vertical axis of the reactor.

Embodiment 12. The system of any of embodiments 1 to 11, further comprising at least one additional support plate positioned to form multiple vertical layers within the interior of the reactor, and the at least one additional support plate engaging the plurality of annular shrouds.

Embodiment 13. The system of any of embodiments 1 10 12, wherein the reactor is a bioreactor.

Embodiment 14. The system of any of embodiments 1 to 12, wherein the reactor is a bioreactor comprising:
a liquid growth medium;
a substrate comprising at least one C1 carbon source, wherein the plurality of spargers are configured to inject substrate bubbles into the liquid growth medium; and
a culture of at least one microorganism in the liquid growth medium, wherein the culture of at least one microorganism anaerobically ferments the substrate to produce at least one fermentation product.

Embodiment 15. A method of sparging bubbles into a liquid comprising:
sparging gas into a reactor containing a liquid via a plurality of spargers positioned within the reactor and configured to emit bubbles;
directing a flow of the liquid across an exterior surface of the spargers via a plurality of annular shrouds within the reactor and surrounding the plurality of spargers; and
shearing the bubbles at a surface of the plurality of spargers via the flow of the liquid across the exterior surface of the spargers.

Embodiment 16. The method of embodiment 15 further comprising accelerating the flow of the liquid across the exterior surface of the spargers via a gap formed between an interior surface of the annular shrouds and the exterior surface of the spargers.

Embodiment 17. The method of embodiment 15 or 16, wherein the accelerated flow of the liquid across the exterior surface of the spargers has a superficial liquid velocity of at least 0.3 m/s.

Embodiment 18. The method of any of embodiments 15 to 17, wherein the accelerated flow of the liquid across the exterior surface of the plurality of spargers has a velocity of about 0.3 m/s to about 10 m/s.

Embodiment 19. The method of any of embodiments 15 to 18, wherein the sheared bubbles have a diameter of about 0.2 mm to about 2.0 mm.

Embodiment 20. The method of any of embodiments 15 to 19, wherein a superficial velocity of a gas phase in the vessel is at least 0.03 m/s.

Embodiment 21. The method of any of embodiments 15 to 19, wherein a superficial velocity of the gas phase in the vessel is about 0.03 m/s to about 0.1 m/s.

Embodiment 22. The method of any of embodiments 15 to 21, wherein the bubbles are substrate bubbles within a bioreactor containing a liquid growth medium, wherein a culture of at least one microorganism in the liquid growth medium aerobically ferments the substrate to produce at least one fermentation product.

The invention claimed is:

1. A reactor and sparger system for injecting bubbles into a liquid comprising:
   a reactor;
   a support plate;
   a plurality of annular shrouds engaged with the support plate; and
   a plurality of spargers positioned within the annular shrouds to define a gap between an interior surface of the annular shroud and an exterior surface of the corresponding sparger:
   a plurality of headers engaged with the plurality of spargers wherein the plurality of spargers are configured to receive a gas supply from the plurality of headers and the plurality of headers further comprise at least one baffle to disperse a fluid comprising the liquid and the bubbles; and
   wherein the support plate, the annular shrouds, and the spargers are positioned within the interior of the reactor.

2. The system of claim 1 wherein the support plate and the annular shrouds are integrated into a single component.

3. The system of claim 1 wherein two or more spargers are positioned within a single annular shroud.

4. The system of claim 1, wherein a length of the spargers is at least 10 cm.

5. The system of claim 1, wherein the gap is from about 1 mm to about 20 mm.

6. The system of claim 1, wherein the support plate, the annular shrouds, and the spargers are positioned at a top portion or at a bottom portion of the reactor.

7. The system of claim 1, wherein the liquid is at least partially recirculated liquid.

8. The system of claim 1, wherein the support plate further comprises a plurality of perforations.

9. The system of claim 1, wherein the annular shrouds are positioned within about 20 degrees of a vertical axis of the reactor.

10. The system of claim 1, further comprising at least one additional support plate positioned to form multiple vertical layers within the interior of the reactor, and the at least one additional support plate engaging the plurality of annular shrouds.

11. The system of claim 1, wherein the reactor is a bioreactor.

12. The system of claim 1, wherein the reactor is a bioreactor comprising:
    a liquid growth medium;
    a substrate comprising at least one C1 carbon source, wherein the plurality of spargers are configured to inject substrate bubbles into the liquid growth medium; and
    a culture of at least one microorganism in the liquid growth medium, wherein the culture of at least one microorganism anaerobically ferments the substrate to produce at least one fermentation product.

* * * * *